(12) United States Patent
Jörger

(10) Patent No.: US 7,637,661 B2
(45) Date of Patent: Dec. 29, 2009

(54) X-RAY IMAGING SYSTEM AND METHOD FOR DEFINING OR CARRYING OUT CALIBRATION PROCESSES

(75) Inventor: Clemens Jörger, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/190,049

(22) Filed: Aug. 12, 2008

(65) Prior Publication Data

US 2009/0046836 A1   Feb. 19, 2009

(30) Foreign Application Priority Data

Aug. 13, 2007  (DE)  ................. 10 2007 038 164

(51) Int. Cl.
*G01D 18/00* (2006.01)
(52) U.S. Cl. .................................... 378/207
(58) Field of Classification Search ............. 378/4, 378/19, 62, 98.8, 196, 197, 205, 207
See application file for complete search history.

(56) References Cited

U.S. PATENT DOCUMENTS 7,474,731 B2 *  1/2009  Spahn ....................... 378/62

* cited by examiner

*Primary Examiner*—Irakli Kiknadze
(74) *Attorney, Agent, or Firm*—King & Spalding L.L.P.

(57) ABSTRACT

X-ray imaging systems can have different modes of operation. There is a calibration process for each mode of operation. Conventionally, the overall system is actuated during the calibration process in exactly the same way as when operating the x-ray imaging system (10) with the associated mode of operation. Individual calibration processes are now restricted to fixing a flat-panel parameter set which matches the mode of operation and by which the flat-panel detector (12) is actuated. However, the remaining system (14) does not have to be actuated depending on the mode of operation associated with the calibration process. A fixed system parameter set which is independent of the mode of operation is sufficient. It has been proven to be sufficient if no machine movements are carried out during all calibration processes, the x-ray radiation generator operates in the two-point technique and a series of images is recorded.

14 Claims, 1 Drawing Sheet

X-RAY IMAGING SYSTEM AND METHOD FOR DEFINING OR CARRYING OUT CALIBRATION PROCESSES

CROSS-REFERENCE TO RELATED APPLICATIONS

This application claims priority to German application number 10 2007 038 164.8 filed Aug. 13, 2007, the contents of which are hereby incorporated by reference in their entirety.

TECHNICAL FIELD

The invention relates to an x-ray imaging system which can be operated in at least two different modes of operation, and also to a method for defining or carrying out a calibration process or calibration processes.

BACKGROUND

X-ray imaging systems of the type mentioned are becoming more widely used. Typically, one mode of operation is radiographic, in which individual images are recorded with a dose ensuring a good image quality, and are stored. Furthermore, fluoroscopy is a mode of operation in which a plurality of images are recorded in series without being stored, with the x-ray dose being lower in fluoroscopy than in radiography. Furthermore, a hybrid mode of operation between fluoroscopy and radiography is known in which the fluoroscopy image sequences are interrupted by the recording of individual images (in the radiography mode). Tomography is a further known mode of operation.

In a more recent system, the same flat-panel x-ray detector and the same x-ray radiation source are used in all modes of operation. These are usually moved together, occasionally also relative to one another, with the aid of an x-ray C-arm, for example, onto which the flat-panel x-ray detector and the x-ray radiation source are attached. A control device controls the movements and the settings of both the x-ray radiation source and also the flat-panel x-ray detector. This means that in every mode of operation the control device must fix at least one control parameter related to the functioning of the flat-panel x-ray detector and, furthermore, it must fix at least one control parameter not related to the functioning of the flat-panel x-ray detector. Presently, those modes of operation which differ in fixing the control parameter not related to the functioning of the flat-panel x-ray detector are the focus of interest. (They regularly additionally differ in the at least one control parameter related to the functioning of the flat-panel x-ray detector used.)

Flat-panel x-ray detectors usually comprise a semiconductor with a scintillator located above it. In the case of flat-panel x-ray detectors, there are inhomogeneities over the entire face of the sensor. These inhomogeneities can be created by defective pixels, nonlinearities in the amplification or different dark currents. The images recorded by the flat-panel x-ray detector should be subjected to a corrective step so that the influence of the inhomogeneities is removed. Thus, the inhomogeneities have to be acquired in some form in advance. This occurs within the scope of a calibration process. By way of example, an image can be recorded without x-ray radiation during the calibration, or image series in which the x-ray radiation intensities are variable can be recorded.

Until now, the calibration process simulated the mode of operation in detail. This means that, during the calibration process, the control parameters not related to the functioning of the flat-panel x-ray detector are regularly fixed in exactly the same manner as when operating the x-ray imaging machine with the associated mode of operation.

By way of example, the so-called x-ray technique is defined for each mode of operation. The zero-point technique, one-point technique, two-point technique and three-point technique are differentiated. In the zero-point technique, the x-ray radiation source is regulated to that dose which was previously used in the fluoroscopy mode. In the one-point technique, the dose is fixed and the system then fixes the tube voltage (in kV) and the duration of the irradiation multiplied by the current strength (in mAs) from this. In the two-point technique, the tube voltage and the mAs-value are respectively individually set as parameters. In the three-point technique, the pulse time, during which the x-ray radiation source radiates, is fixed as a parameter in addition to these two parameters.

Fluoroscopy usually uses the zero-point technique, radiography uses the one-point technique, the two-point technique or the three-point technique. In the hybrid mode, the zero-point technique or one-point technique is used. In tomography, the two-point technique is used, and, as an alternative, a type of one-point technique in which the time is given by the traverse speed and traverse angle.

Machine movement fixes another type of control parameters. In a simplified fashion, the parameter can be defined to fix whether machine movement is taking place at all. Machine movements are possible in fluoroscopy but not in radiography, and hence they are not possible in the hybrid mode either. There are machine movements in tomography.

A further control parameter fixes whether a series of images or individual images are recorded. Image series are recorded in fluoroscopy, individual images in the case of radiography, and series images and individual images are recorded in the hybrid mode. Tomography likewise records individual images.

In the prior art, the control parameters mentioned have the same settings in the calibration process as they would have otherwise. The respective x-ray technique of the mode of operation is used and machine movements take place if they also take place during the mode of operation.

Correspondingly, one or more calibration process possibilities have to be stored in the control device for each mode of operation. These calibration processes are selected by means of an input device. The programming of these multi-faceted calibration processes is very complex. Once the calibration processes have been fixed, it is difficult to carry out a change.

SUMMARY

Fixing and carrying out the calibration processes can be simplified such that the x-ray imaging system can be produced and operated economically.

According to an embodiment, an x-ray imaging system may comprise a flat-panel x-ray detector and a control device, operable to enable the alternative operation of the x-ray imaging system in at least one of two different modes of operation, wherein at least one control parameter related to the functioning of the flat-panel x-ray detector, intended to be sent from the control device to the flat-panel x-ray detector, and at least one control parameter not related to the functioning of the flat-panel x-ray detector, intended to be sent from the control device to a component differing from the flat-panel x-ray detector, are defined for every mode of operation, wherein the modes of operation differ in at least one control parameter not related to the functioning of the flat-panel x-ray detector, wherein the control device furthermore is operable to carry out a calibration process for each mode of operation in which in each case at least one control parameter related to the functioning of the flat-panel x-ray detector and at least one control parameter not related to the functioning of the flat-panel x-ray detector is emitted by the control device, and wherein each control parameter not related to the functioning of the flat-panel x-ray detector respectively emitted during a calibration process is independent of the respective mode of operation with which the calibration process is associated.

According to a further embodiment, the control parameters not related to the functioning of the flat-panel x-ray detector can be used to actuate motors which cause machine movement and/or are used to fix the x-ray technique. According to a further embodiment, at least one control parameter not related to the functioning of the flat-panel x-ray detector may ensure that no machine movements are carried out during all calibration processes. According to a further embodiment, at least one control parameter not related to the functioning of the flat-panel x-ray detector may ensure that an x-ray radiation generator of the x-ray imaging system operates in the two-point technique during all calibration processes. According to a further embodiment, at least one control parameter not related to the functioning of the flat-panel x-ray detector may ensure that a plurality of calibration images are recorded in succession during all calibration processes.

According to another embodiment, a method for defining or carrying out calibration processes using an x-ray imaging system for respectively one of a plurality of modes of operation of the x-ray imaging system, hay comprise the step of supplying at least one control parameter to a flat-panel x-ray detector of an x-ray imaging system and at least one control parameter to at least one component of the x-ray imaging system which differs from the flat-panel x-ray detector by a control device during each calibration process, wherein the calibration processes only differ in that at least one control parameter supplied to the flat-panel x-ray detector is different.

According to a further embodiment, each calibration process may be carried out without machine movements, and/or the x-ray radiation generator may operate in the two point technique during each calibration process, and/or a series of calibration images can be recorded during each calibration process.

According to another embodiment, in an x-ray imaging system having a flat-panel x-ray detector and a control device, operable to enable the operation of the x-ray imaging system in a mode of operation in which machine movements occur and which is furthermore designed to enable the carrying out of a calibration process of the mode of operation, no machine movements may occur during the calibration process.

According to another embodiment, in a method for defining or carrying out a calibration process of a mode of operation of an x-ray imaging system in which machine movements occur, no machine movements may occur during the calibration process.

BRIEF DESCRIPTION OF THE DRAWINGS

In the following text, an embodiment is described with reference to the drawing, with FIG. 1 illustrating how the components interact when inputting a calibrating mode of a first mode of operation on the basis of a schematically illustrated x-ray imaging system, and FIG. 2 illustrating the same when inputting a calibrating mode of a second mode of operation.

DETAILED DESCRIPTION

Figure 1:
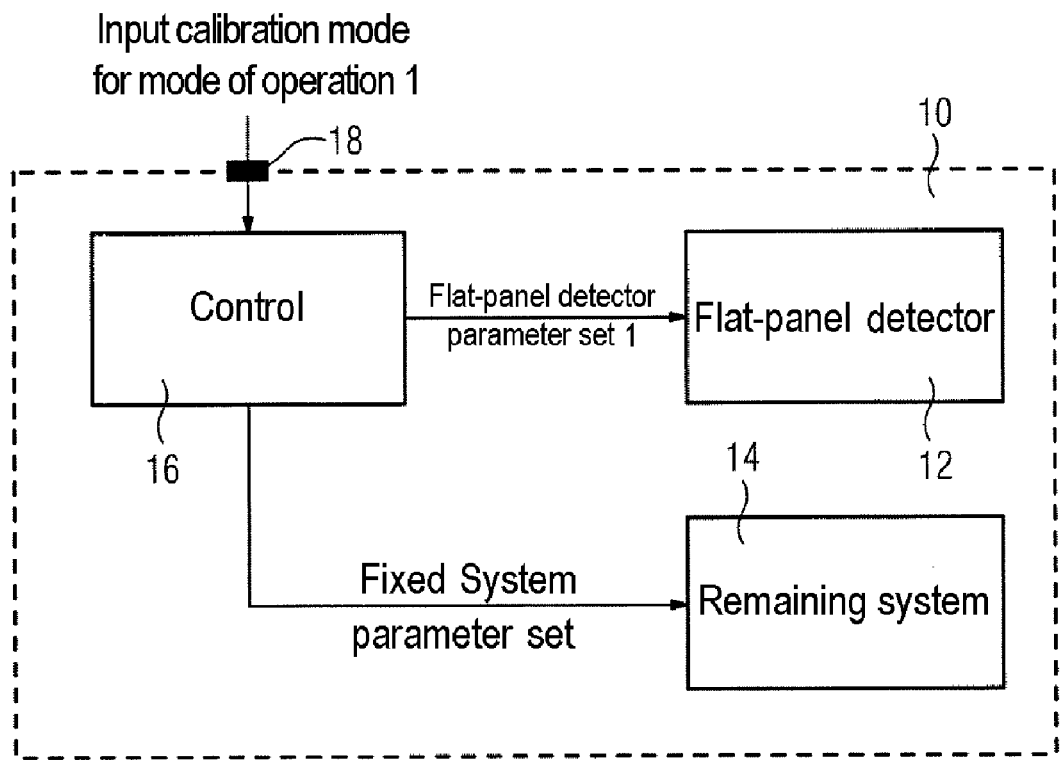

According to various embodiments, each control parameter not related to the functioning of the flat-panel x-ray detector, respectively emitted by the control device during the calibration process, may be independent of the respective mode of operation with which the calibration process is associated.

In other words, the control parameters not related to the functioning of the flat-panel x-ray detector respectively emitted for all calibration processes are identical. Only the control parameters related to the flat-panel x-ray detector are respectively adapted to the mode of operation with which the calibration process is associated.

The various embodiments are based on the recognition that the external conditions during the calibrating process can by all means be different from those of the associated mode of operation. It is a question of acquiring the inhomogeneities of the flat-panel x-ray detector. For this purpose, it suffices in each case only to operate the flat-panel x-ray detector as in the respective modes of operation.

As has already been mentioned above, the control parameters not related to the functioning of the flat-panel x-ray detector are used to actuate motors causing machine movements and/or to fix the x-ray technique. It can now be stipulated that no machine movements at all are carried out during all calibration processes. Furthermore, it can be stipulated that the x-ray radiation generator of the x-ray imaging machine works in the two-point technique during all calibrating processes. Moreover, a plurality of images being recorded in succession can be common to all calibration processes.

It can be advantageous if machine movements are dispensed with. The x-ray technique as a two-point technique can match all modes of operation, and if the calibration images are recorded in series, the series also contains enough individual images which match those modes of operation in which only individual images are recorded.

According to a further embodiment, a method for defining or carrying out calibration processes using an x-ray imaging system can be provided for respectively one of a plurality of modes of operation of the x-ray imaging system. In the method it is provided that both at least one control parameter is supplied to a flat-panel x-ray detector of the x-ray imaging system and at least one control parameter is supplied to at least one component of the x-ray imaging system which differs from the flat-panel x-ray detector by a control device during each calibration process. The method according to an embodiment is characterized in that the calibration processes only differ in that at least one control parameter supplied to the flat-panel x-ray detector is different. Conversely this means that the calibration processes do not differ in the control parameters not supplied to the flat-panel x-ray detector. Exemplary cases were mentioned above.

According to a further embodiment, an x-ray imaging system having a flat-panel x-ray detector and a control device is provided and is designed to enable the operation of the x-ray imaging system in a mode of operation with machine movements occurring and is furthermore designed to enable the carrying out of a calibration process of the mode of operation. This x-ray imaging system is characterized in that no machine movements occur during the calibration process. In this aspect, the machine movements in particular are the focus of interest. As a result of no machine movements occurring during the calibration process, the calibration process can be carried out in a particularly uncomplicated manner and can also be correspondingly prepared, e.g. programmed, in an uncomplicated manner. With regard to this aspect, a method for carrying out a calibration process for a mode of operation of an x-ray imaging system in which machine movements occur is provided. This method is characterized in that no machine movements occur during the calibration process.

An x-ray imaging system, referred to as a whole by 10 in the figures, comprises a flat-panel x-ray detector 12 which is irradiated by an x-ray radiation source. The x-ray imaging system 10 comprises components that can be moved with the aid of motors. The system parts differing from the flat-panel detector 12 are referred to by 14 in the figures, with the exception of the control device 16. The control device controls both the flat-panel detector 12 and also the remaining system 14. By means of an input device 18, schematically indicated as a user interface, the control device 16 can be made to operate the x-ray imaging system in a specific mode of operation, or to carry out a calibration process for a method of operation.

FIG. 1 shows that an input is carried out to the effect that a calibrating mode for mode of operation 1 is set, that is to say a calibration process to prepare to operate the x-ray imaging system 10 in mode of operation 1 is intended to be carried out. The control 16 sends a flat-panel detector parameter set 1 which matches the selected mode of operation to the flat-panel detector 12. The parameter set comprises information regarding the matrix size, the binning of pixels (interconnection of pixels), the amplification factor (depending on magnification) and the image frequency.

The control 16 sends a fixed system parameter set to the remaining system 14. This fixed system parameter set does not, corresponding to its designation, depend on the mode of operation for which the calibration process is intended to be carried out. In the present case, the fixed system parameter set is intended to stipulate that the movable parts of the remaining system do not move, that operation is carried out in the two-point technique, and that a series of images is recorded.

Figure 2:
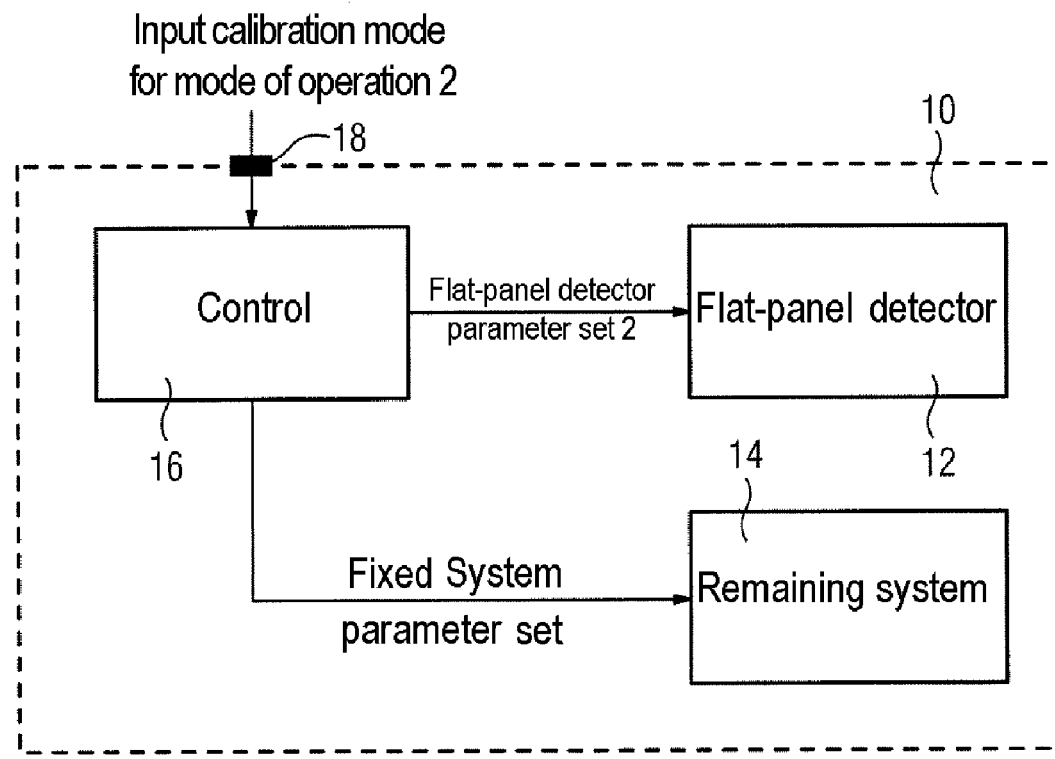

FIG. 2 shows that an input is carried out to the effect that a calibrating mode for mode of operation 2 is set. Now the control 16 sends a flat-panel detector parameter set 2 to the flat-panel detector 12, and this flat-panel parameter set 2 is a flat-panel parameter set matching mode of operation 2. However, nothing changes in the fixed system parameter set: the same system parameter set is sent from the control 16 to the remaining system as in FIG. 1.

What is claimed is:

1. An x-ray imaging system comprising a flat-panel x-ray detector and a control device, operable to enable the alternative operation of the x-ray imaging system in at least one of two different modes of operation, wherein at least one control parameter related to the functioning of the flat-panel x-ray detector, intended to be sent from the control device to the flat-panel x-ray detector, and at least one control parameter not related to the functioning of the flat-panel x-ray detector, intended to be sent from the control device to a component differing from the flat-panel x-ray detector, are defined for every mode of operation, wherein the modes of operation differ in at least one control parameter not related to the functioning of the flat-panel x-ray detector, wherein the control device furthermore is operable to carry out a calibration process for each mode of operation in which in each case at least one control parameter related to the functioning of the flat-panel x-ray detector and at least one control parameter not related to the functioning of the flat-panel x-ray detector is emitted by the control device, and wherein each control parameter not related to the functioning of the flat-panel x-ray detector respectively emitted during a calibration process is independent of the respective mode of operation with which the calibration process is associated.

2. The x-ray imaging system according to claim 1, wherein the control parameters not related to the functioning of the flat-panel x-ray detector are used to actuate motors which cause machine movement or are used to fix the x-ray technique.

3. The x-ray imaging system according to claim 2, wherein at least one control parameter not related to the functioning of the flat-panel x-ray detector ensures that no machine movements are carried out during all calibration processes.

4. The x-ray imaging system according to claim 2, wherein at least one control parameter not related to the functioning of the flat-panel x-ray detector ensures that an x-ray radiation generator of the x-ray imaging system operates in the two-point technique during all calibration processes.

5. The x-ray imaging system according to claim 2, wherein at least one control parameter not related to the functioning of the flat-panel x-ray detector ensures that a plurality of calibration images are recorded in succession during all calibration processes.

6. The x-ray imaging system according to claim 1, wherein the control parameters not related to the functioning of the flat-panel x-ray detector are used to actuate motors which cause machine movement and are used to fix the x-ray technique.

7. The x-ray imaging system according to claim 6, wherein at least one control parameter not related to the functioning of the flat-panel x-ray detector ensures that no machine movements are carried out during all calibration processes.

8. The x-ray imaging system according to claim 6, wherein at least one control parameter not related to the functioning of the flat-panel x-ray detector ensures that an x-ray radiation generator of the x-ray imaging system operates in the two-point technique during all calibration processes.

9. The x-ray imaging system according to claim 6, wherein at least one control parameter not related to the functioning of the flat-panel x-ray detector ensures that a plurality of calibration images are recorded in succession during all calibration processes.

10. A method for defining or carrying out calibration processes using an x-ray imaging system for respectively one of a plurality of modes of operation of the x-ray imaging system, the method comprising the step of:
supplying at least one control parameter to a flat-panel x-ray detector of an x-ray imaging system and at least one control parameter to at least one component of the x-ray imaging system which differs from the flat-panel x-ray detector by a control device during each calibration process, wherein the calibration processes only differ in that at least one control parameter supplied to the flat-panel x-ray detector is different.

11. The method according to claim 10, wherein
each calibration process is carried out without machine movements, or
the x-ray radiation generator operates in the two point technique during each calibration process, or
a series of calibration images are recorded during each calibration process.

12. The method according to claim 10, wherein
each calibration process is carried out without machine movements, and
the x-ray radiation generator operates in the two point technique during each calibration process, and
a series of calibration images are recorded during each calibration process.

13. An x-ray imaging system having a flat-panel x-ray detector and a control device, operable to enable the operation of the x-ray imaging system in a mode of operation in which machine movements occur and which is furthermore designed to enable the carrying out of a calibration process for multiple different modes of operation, wherein no machine movements occur during the calibration process;

wherein, for calibrating each of the multiple different modes of operation, the control device is configured to send (a) a flat-panel detector parameter set specific to that mode of operation to a flat-panel detector, and (b) a fixed system parameter set to other components of the x-ray imaging system, the fixed system parameter set being not specific to any particular mode of operation such that the other components of the x-ray imaging system use the same fixed system parameter set for calibrating each of the multiple different modes of operation.

14. A method for defining or carrying out a calibration process of at least two different modes of operation of an x-ray imaging system in which machine movements occur, wherein no machine movements occur during the calibration process, the method comprising:

for calibration of a first mode of operation, a control device sending (a) a first flat-panel detector parameter set specific to the first mode of operation to a flat-panel detector, and (b) a fixed system parameter set not specific to that mode of operation to other components of the x-ray imaging system; and for calibration of a second mode of operation, the control device sending (a) a second flat-panel detector parameter set specific to the second mode of operation to the flat-panel detector, and (b) the same fixed system parameter set to the other components of the x-ray imaging system.

* * * * *